United States Patent
Anttila et al.

(10) Patent No.: US 7,148,806 B2
(45) Date of Patent: Dec. 12, 2006

(54) ARRANGEMENT IN CONNECTION WITH A PATIENT CIRCUIT AND AN ABSORBER MEANS

(75) Inventors: Mika Anttila, Espoo (FI); Tapani Niklander, Helsinki (FI); Timo Holopainen, Helsinki (FI); Santtu Laurila, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 51 days.

(21) Appl. No.: 10/809,041

(22) Filed: Mar. 25, 2004

(65) Prior Publication Data

US 2005/0211761 A1 Sep. 29, 2005

(51) Int. Cl.
*G09B 23/00* (2006.01)

(52) U.S. Cl. .............. 340/573.1; 340/500; 235/375; 128/205.12; 128/205.28

(58) Field of Classification Search .............. 340/573.1
See application file for complete search history.

(56) References Cited

U.S. PATENT DOCUMENTS

| | | | |
|---|---|---|---|
| 4,958,075 A * | 9/1990 | Mace et al. .................. 250/343 |
| 5,674,381 A | 10/1997 | Den Dekker | |
| 5,694,924 A * | 12/1997 | Cewers .................. 128/204.21 |
| 5,810,001 A | 9/1998 | Genga et al. | |
| 6,131,571 A * | 10/2000 | Lampotang et al. ... 128/204.21 |
| 6,173,711 B1 * | 1/2001 | Ruton ................... 128/204.26 |
| 6,411,199 B1 | 6/2002 | Geistler | |
| 6,626,355 B1 | 9/2003 | Sasse et al. | |
| 2001/0022181 A1 * | 9/2001 | Masson et al. ......... 128/203.12 |
| 2001/0042707 A1 | 11/2001 | Niers et al. | |
| 2002/0023642 A1 * | 2/2002 | Holmsten et al. ...... 128/203.12 |
| 2002/0038392 A1 | 3/2002 | De la Huerga | |
| 2002/0157670 A1 | 10/2002 | Kullik et al. | |

FOREIGN PATENT DOCUMENTS

| | | |
|---|---|---|
| CA | 2 291 375 | 5/2001 |
| DE | 201 13 789 | 6/2002 |
| EP | 1 120 126 | 8/2001 |
| WO | WO-97/10020 | 3/1997 |
| WO | WO-02/05879 | 1/2002 |

OTHER PUBLICATIONS

European Patent Office communication dated Mar. 2, 2006.
Third Part Communication- Protest dated Jan. 17, 2006.

* cited by examiner

*Primary Examiner*—Daniel Wu
*Assistant Examiner*—Eric M. Blount
(74) *Attorney, Agent, or Firm*—Andrus, Sceales, Starke & Sawall, LLP

(57) ABSTRACT

Arrangement in connection with a patient circuit and an absorber means. The arrangement comprises an information transfer means and an electronic means and a transponder electronically programmed with desired information. The transponder is attached to the absorber means. The information transfer means is arranged to communicate with the transponder, and the electronic means is arranged to carry out desired procedures from the basis of the information obtained from the anaesthesia/ventilation system and via the information transfer means from the transponder attached to the absorber means.

17 Claims, 1 Drawing Sheet

ARRANGEMENT IN CONNECTION WITH A PATIENT CIRCUIT AND AN ABSORBER MEANS

BACKGROUND OF THE INVENTION

The invention relates to the use of radio frequency identification (RFID) technique in connection with for example anasthesia/ventilation systems for a patient. A basic RFID system consist of three components, namely an antenna or coil, a transceiver (with decoder) and a transponder (RF tag) electronically programmed with unique information. The transponder can be an RF tag.

The antenna emits radio signals to activate the tag and read and write data to it. Antennas are the conduits between the tag and the transceiver, which controls the system's data acquisition and communication. Antennas are available in a variety of shapes and sizes; they can be built for example into a door frame to receive tag data from persons or things passing through the door, or even mounted on an interstate toll booth to monitor traffic passing by on a freeway. The electromagnetic field produced by an antenna can be constantly present when multiple tags are expected continually. If constant interrogation is not required, the field can be activated by a sensor device.

Often the antenna is packaged with the transceiver and decoder to become a reader (a.k.a. interrogator), which can be configured either as a handheld or a fixed-mount device. The reader emits radio waves in ranges of anywhere from one inch to 100 feet or more, depending upon its power output and the radio frequency used. When an RFID tag passes through the electromagnetic zone, it detects the reader's activation signal. The reader decodes the data encoded in the tag's integrated circuit, for example silicon chip, and the data is passed to the host computer for processing.

RFID tags come in a wide variety of shapes and sizes. Animal tracking tags, inserted beneath the skin, can be as small as a pencil lead in diameter and one-half inch in length. Tags can be screw-shaped to identify trees or wooden items, or credit-card shaped for use in access applications. The anti-theft hard plastic tags attached to merchandise in stores are RFID tags. In addition, heavy-duty 5- by 4- by 2-inch rectangular transponders used to track intermodal containers or heavy machinery, trucks, and railroad cars for maintenance and tracking applications are RFID tags.

RFID tags are categorized as either active or passive. Active RFID tags are powered by an internal battery and are typically read/write, i.e., tag data can be rewritten and/or modified. An active tag's memory size varies according to application requirements; some systems operate with up to 1 MB of memory. In a typical read/write RFID work-in-process system, a tag might give a machine a set of instructions, and the machine would then report its performance to the tag. This encoded data would then become part of the tagged part's history. The battery-supplied power of an active tag generally gives it a longer read range. The trade off is greater size, greater cost, and a limited operational life, which may yield a maximum of 10 years, depending upon operating temperatures and battery type.

Passive RFID tags operate without a separate external power source and obtain operating power generated from the reader. Passive tags are consequently much lighter than active tags, less expensive, and offer a virtually unlimited operational lifetime. The trade off is that they have shorter read ranges than active tags and require a higher-powered reader. Read-only tags are typically passive and are programmed with a unique set of data (usually 32 to 128 bits) that cannot be modified. Read-only tags most often operate as a license plate into a database, in the same way as linear barcodes reference a database containing modifiable product-specific information.

RFID systems are also distinguished by their frequency ranges. Low-frequency (30 KHz to 500 KHz) systems have short reading ranges and lower system costs. They are most commonly used in security access, asset tracking, and animal identification applications. High-frequency (850 MHz to 950 MHz and 2.4 GHz to 2.5 GHz) systems, offering long read ranges (greater than 90 feet) and high reading speeds, are used for such applications as railroad car tracking and automated toll collection. However, the higher performance of high-frequency RFID systems incurs higher system costs.

The significant advantage of all types of RFID systems is the non-contact, non-line-of-sight nature of the technology. Tags can be read through a variety of substances such as snow, fog, ice, paint, crusted grime, and other visually and environmentally challenging conditions, where barcodes or other optically read technologies would be useless. RFID tags can also be read in challenging circumstances at remarkable speeds, in most cases responding in less than 100 milliseconds. The read/write capability of an active RFID system is also a significant advantage in interactive applications such as work-in-process or maintenance tracking. Though it is a costlier technology (compared with barcode), RFID has become indispensable for a wide range of automated data collection and identification applications that would not be possible otherwise.

As suggested earlier, RFID systems are uniquely suited for use in the rigorous rail environment. Field programmable tags permit the full industry standard 12-character identification of each car by type, ownership and serial number. Tags are attached to the vehicle undercarriage; antennae are installed between or adjacent to the tracks, and readers or display devices are typically located within 40 to 100 feet in a wayside hut along with other control and communications equipment. A primary objective in rail applications is the improved fleet utilization that permits reductions in fleet size and/or deferral of investment in new equipment. Commercial truckers are using RFID systems to monitor access and egress from terminal facilities. Combined with weigh-in-motion scales, the same systems can be used for transaction recording at refuse dumps, recycling plants, mines and similar operations, or for credit transactions at truck stops or service depots.

In the plant environment, RF systems are ideally suited for the identification of high-unit-value products moving through a tough assembly process (e.g., automobile or agricultural equipment production where the product is cleaned, bathed, painted and baked). RF systems also offer the durability essential for permanent identification of captive product carriers such as:

Tote boxes, containers, barrels, tubs, and pallets;

Tool carriers, monorail and power, and free conveyor trolleys; and

Lift trucks, towline carts, automatic guided vehicles.

Primary Applications Fall into Two Basic Categories:

Direct product identification wherein the tag specifically identifies the item to which it is attached (e.g., by part number or serial number or, in the case of read/write systems, assembly or process instructions for the item).

Carrier identification where content is identified manually (or with a bar code reader) and fed to the control system along with the carrier's machine-readable RF "license plate number." Subsequent load tracking is accomplished by strategically deployed RF readers.

The automotive industry uses RFID systems to track vehicles through assembly, where tags must perform even after repeated subjection to temperatures of 150 to 200 C, painting, etc. A primary objective for use of the technology in this environment is verification of vehicle identity prior to execution of given assembly tasks. Although manufacturers sequentially track vehicles through assembly, undetected removal of a single vehicle from the line could be costly.

Because RFID tags need not be "seen" to be read, they can be buried within pallets, tote boxes, and other containers and provide solid performance for the life of the carrier. As an example, in a casting operation RF tags are attached to wire baskets which travel through a variety of degreasing, etching and cleaning tanks by means of an overhead power and free conveyor—not a job for optical or magnetic identification media.

In a manner similar to carrier identification, RF tags can be used for tool management. Miniature tags can be placed within tool heads of various types such as block or Cat V-flange, or even within items such as drill bits where individual bits can be read and selected by reader guided robot arms.

RFID systems are used for lift truck and guided vehicle identification in a number of installations. One approach buries tags at strategic locations throughout the facility and verifies vehicle location via on-board DC-powered readers. Other users station readers at the ends of warehouse aisles to monitor lift truck activity. Here, throughput rates permit multiplexing multiple antennae per reader.

The movement and use of valuable equipment and personnel resources can be monitored through RF tags attached to tools, computers, etc. or embedded in credit-card-size security badges. This type of monitoring also provides an extra measure of security for personnel working in high risk areas in case of an emergency evacuation.

Valuable breeding stock, laboratory animals involved in lengthy and expensive research projects, meat and dairy animals, wildlife, and even prized companion animals all present unique identification problems that can be solved by innovative applications of RFID technology.

Referring to the basic principles of anaesthesia/ventilation technique it is important to understand that only a part of the anaesthetic agent inhaled by a patient is absorbed in the alveoli. The excess goes out to the atmosphere. This is both expensive and bad for the environment and one way for better usage of the anaesthetic gases is to re-circulate them to the patient. Oxygen has to be added as well as removal of the carbon dioxide formed by the patient.

In 1777 the chemist Scheele kept bees alive in a glass jar for eight days, absorbing their $CO_2$ with lime water. Soda lime has been used for this purpose for many years in both anaesthetic applications, submarines and scuba diving.

Closed circuit or low flow anesthesia i.e. the circle system, have become the most popular breathing system in the developed countries today.

Just above 5% $CO_2$ is a normal level that is formed in the alveoli during respiration. This level is called the ET $CO_2$ value (end tidal) and the inspiratory level is normally below 0.1%. These two values are normally extracted and displayed from the $CO_2$ curve during a case. Too high levels of $CO_2$ in the lungs will increase the pH value of the blood (acidosis) and will, if not treated, decrease the brain activity.

There are different compositions of soda lime but the main component in all of them are calcium hydroxide $Ca(OH)_2$, also mentioned as slaked lime. Most of the brands also contain NaOH Baralyme consists of 20% barium hydroxide $Ba(OH)2$ and 80% $Ca(OH)_2$.

$$CO_2 + H_2O \leftrightharpoons H_2CO_3 \qquad 1.$$

$CO_2$ in the circuit is absorbed by the water in the soda lime and forms carbonic acid.

$$2H_2CO_3 + 2NaOH(\text{or KOH}) \leftrightharpoons Na_2CO_3(\text{or } K_2CO_3) + 2H_2O + \text{energy} \qquad 2.$$

Carbonic acid reacts with the hydroxides and form carbonates (sodium or potassium carbonate), water and energy (heat).

$$Na_2CO_3(\text{or } K_2CO_3) + Ca(OH)_2 \leftrightharpoons 2NaOH(\text{or KOH}) + CaCO_3 \qquad 3.$$

These carbonates continue the reaction with the calcium hydroxide and forms calcium carbonate, also mentioned as chalk, and the alkali hydroxides.

Out from these reactions we can draw the following conclusions:
1. Water is needed to start the reaction.
2. Potassium or sodium hydroxide is used as a catalyst (not as a real catalyst since a catalyst never takes part of the reaction) since it is reformed during the reaction.
3. The energy and water formed during the second reaction can easily be detected during a case.
4. When the calcium hydroxide is consumed, the alkali bases will not be re formed and the pH will be decreased.

The decrease of pH is indicated with a dye e.g. ethyl violet (white to violet) or Mimosa Z (pink to white) to make the usage visible as a color change. This color change is however not 100% reliable since the pH can increase after some hours when the calcium hydroxides in the inner part of the soda lime granules reacts slowly and forms sodium and potassium hydroxide.

A fresh soda lime have a pH of 12 to 14 and when exhausted the pH decreases to below 10.3, which is the pH where the dye changes from white to violet. According to Dr Mike Clarke at Molecular Products, the average pH of a fully exhausted absorber is below 10. In Canada there is an upper limit of pH 12 of waste to be disposed as non hazardous material.

Datex-Ohmeda is selling soda lime from Molecular Product under the brand name Medisorb. Medisorb is identical to Molecular Products own brand, Sofnolime.

Absorbers/ventilation systems known in the prior art have certain problems, which can be described as follows. Sevofluran can react with soda lime or Baralyme and forms a nephro toxic substance called Compound A.

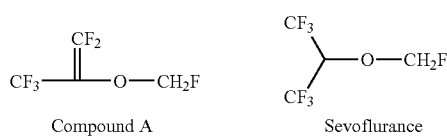

Compound A          Sevoflurance

There are several causes that increase the risk of Compound A forming:
1. Low fresh gas flow. This will increase the temperature and the concentration in the absorber. FDA recommends using higher fresh gas levels than 2 liter per minute to avoid Compound A.

2. Use of Baralyme has shown to produce more Compound A than conventional soda lime.
3. High concentrations of Sevoflurane increase the risk.
4. High temperatures in the soda lime.
5. Dry soda lime
6. KOH in the Soda lime.

Medisorb is KOH free and does not form as much Compound A as e.g. Baralyme or soda lime with KOH.

Carbon monoxide, CO, is a very toxic substance that binds to the hemoglobin at the oxygen sites and and reduces the ability to transport oxygen to the body. Loss of consciousness and death may result from exposure to concentrations of 4000 ppm and higher.

CO is formed in the absorbent material in higher or lower concentrations, depending on:
1. Dry soda lime increases the formation. This phenomena is also called "Monday morning effect" because of cases when the absorber is left with flushing dry gas over the weekend and that the problem was seen during startup on Monday morning.
2. Use of Baralyme has shown to produce more CO than conventional soda lime.
3. High temperatures in the soda lime.

High concentrations of anaesthetic agent in order Desflurane, Enflurane Isoflurane.

Soda lime has to contain some water (>12%) to keep the functionality and to avoid CO and Compound A formation. It is therefore important that the ports of the compact absorbers are sealed.

Formic acid and formalin has been detected from soda lime reactions with Sevoflurane.

In the prior art absorbers the end users have problems in estimating the time of usage. Absorber's capacity is related to the way of usage. The CO2 production of patients can vary, hence the Absorber absorbs different amounts of CO2/time unit. The higher the absorbance is/time unit, the less capacity the absorber has. This is due to the capability of the absorber to absorb. Normally the end user will see the rising of FiCO2 value when the absorber capacity is nearly finished and use this as an indicator to change absorber.

SUMMARY OF THE INVENTION

The object of the present invention is to provide an arrangement and an absorber with which the problems of the prior art can be eliminated. This is achieved with the present invention.

The primary advantage of the present invention is when the invention is used the system will alarm or indicate the particular absorber should not be used, i.e. the problems concerned with the time of usage of the absorbers are eliminated.

BRIEF DESCRIPTION OF THE DRAWINGS

The invention will be described in greater detail below by means of an embodiment shown in the accompanying drawing, in which.

DETAILED DESCRIPTION OF THE INVENTION

Figure 1:
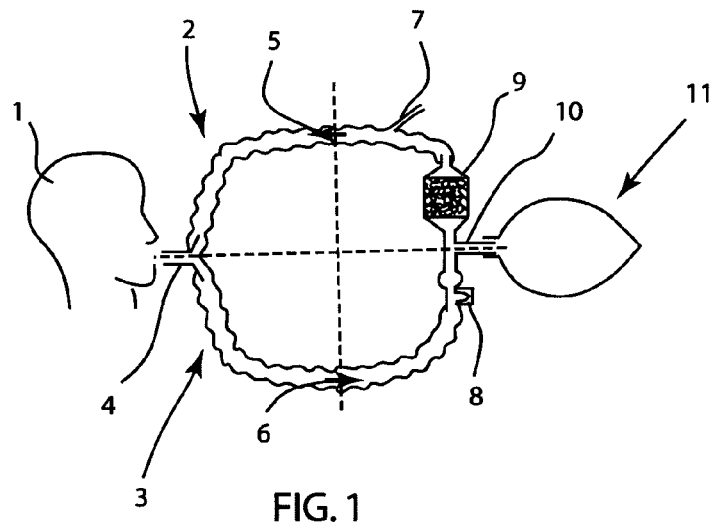
FIG. 1 shows the basic principle of a closed circuit breathing system and FIG. 2 shows schematically one embodiment of the invention.

FIG. 1 shows the basic principle of a closed circuit breathing system. Reference number 1 shows a patient and reference number 2 shows an inspiratory limb of the system and reference number 3 shows respectively an expiratory limb. Reference number 4 shows a Y-piece. Reference numbers 5 and 6 show an inspiratory valve and expiratory valve respectively. Reference number 7 shows a fresh gas inflow site and reference number 8 shows a pop-off valve for excess gas. Reference number 9 shows a CO2 absorber. Reference number 10 shows a bag mounting T-piece and reference number 11 generally a bag side of the system.

The principle of the circuit shown in FIG. 1 is generally known for a person skilled in the art, and therefore said features are not described in detail here.

Figure 2:
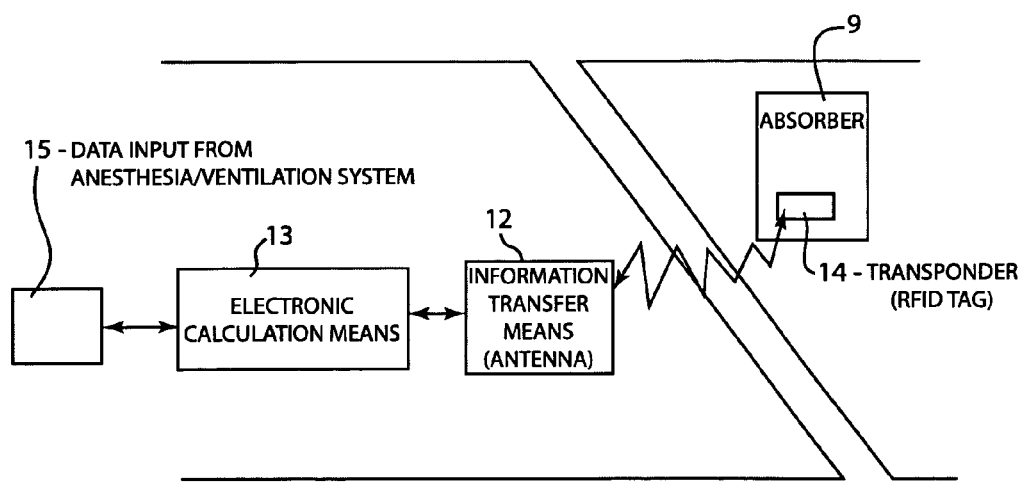

In the present invention the time of usage of an absorber means and other problematic issues are handled with RFID technology. FIGS. 1 and 2 show the basic principle of the present invention.

The present invention relates to an anaesthesia/ventilation system for a patient. The system comprises means 2 for flowing inspiratory gas to the patient 1 and means 3 for flowing expiratory gas flow from the patient 1 to an absorber means 9 and further through the absorber means back to the inspiratory flow. These features are shown schematically in FIG. 1.

The arrangement of the invention comprises an information transfer means 12, an electronic means 13 and a transponder 14 electronically programmed with desired information, e.g. with identification and other information. The transponder 14 is attached to the absorber means 9. The information transfer means 12 is arranged to communicate with the transponder 14, and the electronic means 13 is arranged to carry out desired procedures, e.g. calculations from the basis of the information obtained from the anaesthesia/ventilation system and the information obtained via the information transfer means 12 from the transponder 14 attached to the absorber means 9. The information transfer means 12 can be for example an antenna means and the transponder 14 can be for example an RFID tag. The electronic means 13 can be for example an appropriate processor having software or being able to use software capable of carrying out calculations mentioned above.

One embodiment of the arrangement of the invention is described schematically in FIG. 2. The Absorber 9 is equipped for example with RFID tag 14 that contains information such as:
Identification
Capacity (for instance percent of total amount)
LOT/Serial number
Expire date The anaesthesia machine is provided with the antenna 12, electronic means 13 and appropriate software. The software calculates the consumption of the absorber in question using data from the anaesthesia monitor and ventilator (Fresh Gas Flows, $VCO_2$ values, Minute Volumes, $FiCO_2$ and other possible parameters). The data from the anaesthesia monitor and ventilator is shown with reference number 15 in FIG. 2. The antenna 12 that is based on the side of the anaesthesia workstation, near the absorber 9, is able to write the data in the RFID tag or alternatively to read the data in the RFID tag and to write the data into the RFID tag, for example to subtract the capacity of the absorber 9 from the basis of the values obtained as a result of the use. The values of current absorber capacity in percents can be given on a monitor screen. The arrangement is also capable to calculate a forecast for usage percent/minute and give said information to the user for example on the same monitor screen.

While the RFID tag 14 carries unique information of the absorber means 9 many benefits can be achieved. The RFID tag 14 can for example have expire date written on it. When end users connect a new absorber to the anaesthesia workstation, the system will read the information on the RFID tag 14. If the expire date has passed, the system will alarm or indicate the user that the particular absorber should not be used.

With the RFID system the processor calculates the rate of usage by reading and writing the RFID tag 14 information. The absorbance rate ml of $CO_2$/minute determines the total capacity of the absorber. The actual capability of an absorber 9 can vary between 120 L and 180 L pending on the absorbance rate.

The processor is able to tell the RFID tag 14 that by which rate the absorber 9 is consumed. Users see this as percentage of capacity left/capacity used. When Fresh Gas Flows, Respiratory Rates, Tidal Volumes and $CO_2$ production (patients) vary the system calculates real time absorbance rate and the users see percentage of used capacity/capacity left.

With this real time information of usage the anaesthesia workstation users have a forecast for the time that the absorber has left with given parameters (FGF, TV, RR, $VCO_2$).

When a operation starts the anaesthesia workstation users can see how much capacity the absorber 9 has left and can choose to change the absorber, this way they do not have to change the absorber in the middle of an operation.

When the absorber 9 is nearly finished alarms will indicate that absorber has been almost totally consumed and should be replaced with a new one. Once the absorber has been used fully, the RFID tag 14 contains the usage history and prevents re-use. If a fully used absorber 9 is connected to an anaesthesia workstation the system will give alarm "totally used".

Carbon monoxide, CO, formation can be prevented by preventing the drying of soda lime. The RFID tag 14 in the absorber contains information of usage. The so called "Monday morning effect" will be prevented by using an alarm indicating that the absorber has been flushed with dry gas over a long time, for example over a weekend.

With RFID system there is no need for color change observation and no need for rough estimations or guesses. The invention will give real time indication on the real usage of the absorber. The problems with the color change can be avoided by using a processor that is shown on the anaesthesia monitor/ventilator. The fact that the color change is not permanent does not matter, because the RFID tag 14 contains the information of usage history. If the absorber is once used up, an alarm will indicate that absorber should not be used. The color change does not normally change color "all the way" in other words when the soda lime is exhausted, the entire absorber has not changed color. This will not be a problem because the arrangement of the invention will now indicate percentage of capacity used/left.

The invention is described above by using one embodiment of the invention. The invention is however not restricted to said embodiment alone but the invention can also be applied otherwise and also in other systems. The embodiment shown in FIG. 2 uses a wireless connection. It is however quite possible within the spirit of the invention to use a wire connection between the transponder and the electronic means. The invention can also be used in identification of patient circuits. The workstation could detect/identify what kind of circuit is attached to it, and also to detect if the circuit itself is correctly connected. System could then set itself according to circuit, for example pediatric parameters vs. adult parameters of ventilation. In Disposable accessories the system could identify when accessories are reused. The invention can also be used in following pressure drop changes (pressure difference) of heat and moisture exchangers and filters. The system could alarm when the pressures increase due to blockage or excess humidity (water). The invention can also be used so that the hospitals will be able to bill customers/case/used accessories. Hospitals and other customers will be able to manage their inventories with the invention.

The invention claimed is:

1. An arrangement for use with an anesthesia/ventilation system for a patient, the system including a breathing circuit for supplying breathing gases to the patient for respiration, said breathing circuit having means for flowing inspiratory gas to the patient and means for flowing expiratory gases from the patient through a $CO_2$ absorber means back to the inspiratory gas flow means, the arrangement comprising:
   a transponder attached to the absorber means and electronically programmed with desired information including information relating to a $CO_2$ absorption characteristic of the absorber means;
   an electronic information transfer means arranged to communicate with said transponder; and
   electronic computation means, said electronic computation means being couplable to the anesthesia/ventilation system for receiving information relating to the amount of $CO_2$ introduced in the breathing circuit in the course of respiration by the patient, said electronic computation means receiving information from said transponder, via said electronic information transfer means, relating to a $CO_2$ absorption characteristic of the absorber means and performing a calculation to make a determination relating to the absorption of $CO_2$ by the absorber means.

2. The arrangement of claim 1, wherein said electronic computation means makes an identification of the absorber means.

3. The arrangement of claim 1, wherein the electronic information transfer means comprises an antenna means, and that the antenna means is arranged to read the information programmed in the transponder.

4. The arrangement of claim 3, wherein the antenna means is arranged to feed information calculated in the electronic computation means to the transponder.

5. The arrangement of claim 1, wherein the electronic information transfer means comprises a wire connection between the electronic information transfer means and the transponder.

6. The arrangement of claim 5, wherein the wire connection is arranged to feed information determined in the electronic computation means to the transponder.

7. The arrangement of claim 3, wherein the antenna means is a RFID antenna and the transponder is an RFID tag.

8. The arrangement of claim 4, wherein the antenna means is a RFID antenna and the transponder is an RFID tag.

9. The apparatus of claim 1 wherein said electronic computation means is further defined as using information received from the transponder relating to the $CO_2$ absorption capacity of the absorber means and information received from the anesthesia/ventilation system to make a determination of a current absorption capacity of the absorber means.

10. The arrangement of claim 9 wherein said electronic computation means makes a determination of one of the capacity of the absorber consumed or the capacity of the absorber remaining.

11. The arrangement of claim 9 wherein said electronic computation means makes a determination of the current absorption capacity of said absorber means as a percentage absorption capacity remaining or a percentage absorption capacity used up.

12. The arrangement of claim 1 wherein said electronic computation means uses information received from said transponder relating to the $CO_2$ capacity of the absorber means and information received from the anesthesia/ventilation system to determine the rate at which $CO_2$ is being absorbed by said absorption means, and determines the time remaining until the absorber means reaches its capacity for absorption.

13. The arrangement of claim 1 wherein said electronic computation means is further defined as using information received from the anesthesia/ventilation system comprising one or more of $VCO_2$ (rate of $CO_2$ production), fresh gas flow, minute volume, tidal volume, $FiCO_2$ (fractional inspired $CO_2$), and respiration rate.

14. The arrangement of claim 9 wherein said electronic computation means is further defined as using information received from the anesthesia/ventilation system comprising one or more of $VCO_2$ (rate of $CO_2$ production), fresh gas flow, minute volume, tidal volume, $FiCO_2$ (fractional inspired $CO_2$), and respiration rate.

15. The arrangement of claim 12 wherein said electronic computation means is further defined as using information received from the anesthesia/ventilation system comprising one or more of $VCO_2$ (rate of $CO_2$ production), fresh gas flow, minute volume, tidal volume, $FiCO_2$ (fractional inspired $CO_2$), and respiration rate.

16. The arrangement of claim 1 wherein said electronic computation means makes a determination of the periods of use of the absorber means.

17. The arrangement of claim 16 wherein said electronic computation means makes a determination of periods of exposure of the absorber means to dry flushing gases.

* * * * *